(12) United States Patent
Schulte et al.

(10) Patent No.: US 8,010,378 B2
(45) Date of Patent: Aug. 30, 2011

(54) METHOD AND SYSTEM FOR DETECTING AND ANALYZING CLINICAL PICTURES AND THE CAUSES THEREOF AND FOR DETERMINING PROPOSALS FOR APPROPRIATE THERAPY

(75) Inventors: Martin Schulte, Moelln (DE); Marion Norden, Glinde (DE); Joachim Ganzer, Hamburg (DE)

(73) Assignee: Merck Patent Gesellschaft Mit Berschrankter Haftung, Darmstadt (DE)

( * ) Notice: Subject to any disclaimer, the term of this patent is extended or adjusted under 35 U.S.C. 154(b) by 539 days.

(21) Appl. No.: 10/518,433

(22) PCT Filed: Jun. 14, 2003

(86) PCT No.: PCT/EP03/06299
§ 371 (c)(1),
(2), (4) Date: Jun. 7, 2005

(87) PCT Pub. No.: WO04/001665
PCT Pub. Date: Dec. 31, 2003

(65) Prior Publication Data
US 2005/0234306 A1    Oct. 20, 2005

(30) Foreign Application Priority Data
Jun. 20, 2002    (DE) .................................. 102 27 542

(51) Int. Cl.
*G06Q 10/00* (2006.01)
(52) U.S. Cl. ............................. 705/2; 600/300; 128/920
(58) Field of Classification Search .................. 600/300, 600/301; 128/903–905, 920; 705/2, 3
See application file for complete search history.

(56) References Cited

U.S. PATENT DOCUMENTS

| 5,473,537 | A | | 12/1995 | Gray et al. |
| 5,572,421 | A | | 11/1996 | Turcotte, II et al. |
| 5,660,176 | A | * | 8/1997 | Iliff .............................. 600/300 |
| 5,868,669 | A | * | 2/1999 | Iliff .............................. 600/300 |
| 6,113,540 | A | * | 9/2000 | Iliff .............................. 600/300 |
| 6,270,456 | B1 | * | 8/2001 | Iliff .............................. 600/300 |
| 6,288,646 | B1 | * | 9/2001 | Skardon ....................... 340/627 |
| 6,607,482 | B1 | * | 8/2003 | Teitelbaum .................. 600/300 |
| 2001/0012913 | A1 | | 8/2001 | Iliff |
| 2001/0053875 | A1 | | 12/2001 | Iliff |
| 2002/0029157 | A1 | * | 3/2002 | Marchosky ...................... 705/3 |
| 2002/0038227 | A1 | * | 3/2002 | Fey et al. ........................ 705/3 |
| 2002/0044296 | A1 | | 4/2002 | Skaanning |
| 2005/0108051 | A1 | * | 5/2005 | Weinstein ....................... 705/2 |

OTHER PUBLICATIONS

Gideon, Copyright 1994—2002 Gideon Informatics, Inc.; http://web.archive.orarweb/20020531173951/http://www.gideononline.com/ pp. 1-12.

* cited by examiner

*Primary Examiner* — Sam Yao
*Assistant Examiner* — Kai Rajan
(74) *Attorney, Agent, or Firm* — Millen, White, Zelano, Branigan, P.C.

(57) ABSTRACT

The invention relates to a method for detecting and analyzing clinical pictures and the causes thereof and determining appropriate therapy proposals. The invention is a system for detecting and analyzing clinical pictures and the causes thereof and for determining proposals for appropriate therapy, which can lead to a diagnosis and a corresponding therapy proposal even in the case of complex clinical causes and pictures, said proposal involving a maximum diagnostic certainty and minimum risk for the patient.

12 Claims, 5 Drawing Sheets

Anamnesis result
  Result of individual anamnesis:
  • Maximum discomfort January to April: Suspected pollen allergy
  • Reference to circadian exposure
      Allergens:
      Clinical relevance: high
  • Birch, weeping
  • Hazel, common
      Clinical relevance: average
  • Alder, black
  • Euroglyphus maynei: house dust mite
      Clinical relevance: low
  • Beech, red
  • Oak, English
  • Elm, wych
      Cross allergens:
  • Apple
  • Pear
  • Curry
  • Ash, common
  • Hornbeam
  • Hazelnut
  • Carrot
  • Chestnut
  • Kiwi
  • Peach
  • Celery
  • Tomato

Anamnesis result    Result of individual anamnesis:

- Maximum discomfort January to April: Suspected pollen allergy
- Reference to circadian exposure

Allergens:
- Birch, weeping        Clinical relevance: high
- Hazel, common

- Alder, black          Clinical relevance: average
- Euroglyphus maynei: house dust mite
                        Clinical relevance: low
- Beech, red
- Oak, English
- Elm, wych

Cross allergens:
- Apple
- Pear
- Curry
- Ash, common
- Hornbeam
- Hazelnut
- Carrot
- Chestnut
- Kiwi
- Peach
- Celery
- Tomato

Diagnosis proposal:

| Code | Allergen | Anamnesis | Prick | Intracutan. | BPT | KPT | NPT | EAST | Allergodip | Diagnos |
|------|----------|-----------|-------|-------------|-----|-----|-----|------|------------|---------|
| 108 | Birch Reference to cross-allergenity | Pollen allergy (mite/ mildew allergy also possible) | +++ (P) | | | | | 4 | | ☐ Pollen allergy with birch (J30.1) |
| 115 | Alder | Pollen allergy (mite/ mildew allergy also possible) | +++ | | | | | 4 | | ☐ Pollen allergy with alder (J30.1) |
| 129 | Hazel | Pollen allergy (mite/ mildew allergy also possible) | +++ (P) | | | | | 5 | | ☐ Pollen allergy with Hazel (J30.1) |

Export   Print   Close

FIG. 5

METHOD AND SYSTEM FOR DETECTING AND ANALYZING CLINICAL PICTURES AND THE CAUSES THEREOF AND FOR DETERMINING PROPOSALS FOR APPROPRIATE THERAPY

The present invention relates to a method and a system for the recording, analysis and diagnosis of syndromes and their causes and for establishing suitable therapy proposals.

The method and the system operate with computer assistance and using corresponding databases each of which are created as a part of the method and system or else are already available and can be supplemented, and which optionally may also be available to the public. A particular possible application of the present invention is in the field of the diagnosis and therapy of allergies.

Diagnosis systems are already known which are based on a computer-assisted database search in which [the] doctor can enter one or more specifically recorded symptoms, whereupon the system concerned searches for diagnoses which match the symptoms.

These systems are generally still relatively inadequate, as they ultimately depend on which symptoms a patient directly reports to a doctor of his own -accord or which the doctor establishes through appropriate examination. In addition a specific syndrome and the diagnosis produced on the basis of the recorded symptoms can often have very different causes which can only be determined very inadequately, if at all, with the conventional systems. In particular in the field of allergic illnesses, the search for a cause often proves exceptionally difficult, since in the rarest cases the illness is triggered by just a single allergen [thus] it is necessary to take into consideration all possible allergens. Potential cross-reactive allergens can play an important role.

Although in certain circumstances, through targeted questioning a doctor can learn and evaluate further information and further aspects of the symptomatics, this depends to a large extent on the experience, creativity and associative powers of the doctor concerned. Due to the wealth and complexity of the possible interactions, an individual is also not as a rule able to determine, through targeted questions, all the possible combinations which come into consideration for a specific syndrome.

Compared with this state of the art, the problem on which the present invention is based is to create a method and a system for the recording and analysis of syndromes and their causes and for the establishing of suitable therapy proposals, which, even when there are very complex causes of illness and symptoms, lead to a diagnosis and a corresponding therapy proposal which bring about maximum certainty of diagnosis and minimum risk as regards the appropriate therapy for the patient.

As regards the method, this problem is solved by the features set out in claim 1.

As regards the system, the problem forming the basis of the invention is solved in the features set out in claim 11.

The essential features of the present invention comprise the following steps:

a) Preparing at least one set of anamnesis questions and storing this set in a data memory,
b) Preparing a set of data relating to the causes of diseases and storing this set in a data memory,
c) Providing a computer program which selects and presents anamnesis questions according to a predetermined set of rules,
d) Recording the answers to the anamnesis questions,
e) Creating a set of possible diagnoses on the basis of the answers which have been recorded in step d) and optionally creating examination or test proposals to further narrow down the diagnosis,
f) Preparing one or more diagnosis proposals and
g) Preparing one or more therapy proposals, with steps e) to g) in particular proceeding automatically under the control of an interactive computer program.

While preparing the set of anamnesis questions which is stored in a suitable file or a data memory of a computer system, all of the current scientific knowledge can be combined without being limited to the knowledge of an individual doctor and his current powers of recollection. This leads to a very extensive and (theoretically) complete set of anamnesis questions which, although not necessarily applied in its entirety to an individual patient, does however in principle cover all the conceivable and all the known illnesses recorded in the scientific literature which covers illnesses to be diagnosed with the relevant method. It is understood that the set of anamnesis questions can perfectly well be limited to a specific medical field of expertise such as for example allergology.

Furthermore, according to the invention a set of data relating to causes of diseases is created and this set is also stored in a data memory of a computer. It is understood that the set of anamnesis questions and the set of causes of diseases are matched such that each cause of disease actually recorded in the set of causes of diseases or symptoms resulting from same can also be retrieved directly or indirectly with the set of anamnesis questions.

Also, the set of data relating to causes of diseases has a scope which reflects the current state of scientific knowledge, it being understood that in an individual patient only a tiny fraction of the causes of diseases stored overall is into consideration.

A feature of the present invention is the provision of a computer program which selects and presents anamnesis questions according to a quite specific set of rules which makes the selection and presentation of further questions dependent on the answers to previous questions or on the input of preliminary information. Only in this way is it possible to restrict the comprehensive set of anamnesis questions to an extent which is justifiable in practice and yet still leaves no gaps, if possible, when seeking the causes of an actually existing illness.

There are for example gender- and/or age-specific questions which of course do not need to be asked if, according to the correspondingly inputted preliminary information, the patient in question does not fall into the age category concerned or does not belong to the corresponding gender for whom the said questions are specific. In addition, answers to specific questions, again in taking account of further details, such as for example the preliminary information or other questions already answered, include the answers to specific additional questions or render them obsolete for other reasons. Other answers for their part suggest quite specific additional questions, such as for example in the case of food allergies where, after an introductory question relating to gastrointestinal disorders, detailed questions are asked to narrow the possible food. It is precisely these supplementary questions, aimed at establishing the possible causes of diseases in the case of allergies or also of contraindications and possible interactions, that should and must be asked and clarified as fully as possible. Since, due to the set of rules implicitly contained within it, the computer program links together the logical connections of all the questions and allows or presents only the questions which are actually necessary to clarify a syndrome and, as far as all the remaining questions are concerned, in particular also those which are superfluous in light of logical connecting of answers already given, does not ask them or does so at most as a safeguard and check, the total number of questions is reduced to a reasonable extent, yet all the other conceivable important information which is important for a diagnosis and/or a therapy proposal is still recorded.

For example, this computer program module can also establish the trend of a diagnosis and a corresponding therapy as individual anamnesis questions are still being answered or after the corresponding answers have been inputted, take account of medicinal products that are possibly to be used in such a therapy, and can therefore already also immediately ask questions about possible contraindications and/or incompatibility of medicinal products, so that specific therapies already becoming apparent during the anamnesis are ruled out or preferred.

The answers to the anamnesis questions are recorded and entered into a computer and form a set of data belonging specifically to a patient. On the basis of this set a set of possible diagnoses is created and examination or test proposals are optionally also created in order to better narrow down the diagnosis, in particular if, on the basis of the symptomatics and the answered questions, several different diagnoses suggest themselves or prove possible. After manual and/or automatic recording of the examination or test results, a proposed diagnosis (optionally even several suggested diagnoses) is prepared on the present basis and on one or more therapy proposals are again based on same.

All these last-named steps after the inputting of the answers to the anamnesis questions proceed automatically under the control of an interactive computer program. The computer program is therefore preferably interactive, because then it is possible that the doctor in attendance can, on the basis of his additional practical experience and his responsibility, himself make a selection from among the proposed diagnoses and/or therapies and eliminate or also prefer one or the other. Furthermore it is possible in principle that the patient himself inputs the answers into the computer which presents him with the individual questions in succession, without the doctor's assistance being required, possibly apart from initial directions.

Additional questions can optionally also be created by the doctor and answered by the patient.

Therefore, with the method according to the invention and the corresponding system, the doctor also retains his complete freedom to decide and responsibility, but is assisted by the anamnesis questions selected on the basis of preliminary information and continuously inputted answers in optimised manner according to a predeterminable set of rules that preferably can also be altered or adjusted, which not only saves time but above all also dramatically improves the accuracy of the proposed diagnoses and therapies.

The corresponding system for recording and analyzing syndromes and their causes and for establishing suitable therapy proposals comprises a) a data memory with a stored set of anamnesis questions,
b) a stored set of data relating to causes of diseases, including pathogenic and/or allergenic substances,
c) a computer with a computer program which evaluates and presents anamnesis questions according to a predeterminable set of rules,
d) an input device for the inputting of patient data and answers to the anamnesis questions,
e) a storage device for the inputted data,
f) a computer program which processes the inputted data for the purpose of creating one or more diagnoses and one or more therapy proposals and
g) an output device for the presentation of the questions, the diagnoses and/or therapy proposals It is understood that the whole method and the whole system can consist of a unitary computer program or several program modules. For example it would be possible to use only the anamnesis module which selects and presents the anamnesis questions on the basis of the preliminary information contained in answers already given, or only the diagnosis and therapy module can be used if it is wished to evaluate already available anamneses which have possibly been created, not at all or at an earlier time with the anamnesis module.

A method is particularly preferred in which the recorded preliminary information includes at least the age and gender of a patient and optionally further general features such as for example the principal symptoms, affected organs and/or other, already diagnosed illnesses.

Furthermore, the anamnesis questions should also include questions relating to the time of occurrence, the severity of symptoms and the environmental exposure of the patient.

A variation of the method according to the invention is preferred in which step b) of the preparing of a set of data relating to causes of diseases also includes a listing and storage of allergens.

In addition, a method according to the present invention is preferred in which point values are awarded to at least some part of the answers to the anamnesis questions recorded in step d). In a preferred variation of the method these point values can also be added or multiplied together from specific answers or groups of answers in order to create total point values for a group of answers and/or the entire anamnesis. The anamnesis answers can be at least partly predetermined in discrete selection steps. In a simple case these would be questions which are to be answered with yes/no, and in the case of questions in which for example the severity of a symptom is asked, a multi-step scale can be provided into which the respective answers are sorted.

Depending on which group of answers exceeds a specific point value according to this method, a corresponding diagnosis and a therapy proposal resulting from it is assigned to it. However, test proposals may also be made beforehand by the computer program according to the invention in order to further narrow the suggested diagnoses and therapies.

A system according to the present invention is particularly preferable in which a storage device is provided in which all the data recorded from patients are supplied in anonymized form. Such a storage device can also be made accessible to specifiable user groups if required and the anamnesis results of a large number of patients can be stored centrally there so that these data offer a very good basis for a statistical evaluation. In addition, after diagnosis proposals and treatments have been established, the treatment sequence and the definitive diagnoses can also be inputted into this system so that, in particular, it becomes possible, by comparing later answers to anamnesis questions with already stored answers and the corresponding diagnoses and treatments, to even more quickly and successfully determine a certain diagnosis and supply a corresponding treatment possibility.

Expediently the system according to the invention offers access to a database with possible causes of diseases which among others also includes allergens. This database can be integrated into the system, i.e. formed by a local storage device in which the allergen data or general data relating to causes of diseases are stored and to which the computer program concerned has an access possibility. However it can also be a central database containing causes of diseases which can be accessed by a large number of users with the corresponding programs.

Analogously to the method according to the invention the computer program of the system according to the invention has a scale valuation and combination of the scale valuation of individual answers.

Further advantages, features and possible applications of the present invention are made clear by means of the following description of a version and of the associated overview tables which correspond to specific screen masks.

FIG. 1 is an overview table of an anamnesis result,

FIGS. 2 to 5 are screen displays in the form of file cards for a test proposal, a patient questionnaire, a test result and a diagnosis proposal.

ALLERGY EXPERT SYSTEM

Figure 4:

Immunology and with it allergology are experiencing an enormous development process. New clinically relevant allergens repeatedly take shape, scientific knowledge constantly increases. It is scarcely possible to keep track of such a variety. A doctor active in allergology is required to prepare the correct therapy concept from a large number of possible sensitizations; complexity of anamnesis, diagnosis, therapy and prevention requirements thus increase constantly.

The long-term success of the therapy can be ensured only through high-quality, comprehensive and complete deployment of the instruments of anamnesis, diagnosis and therapy. From the large number of allergens, a structured, complete anamnesis reveals those necessary to a diagnosis for testing. All the clinically relevant allergens with the corresponding cross-reactivities must be borne in mind. The success of the therapy derived from the diagnosis is decisively dependent on the implementation.

The Allergy Expert System (ALEX) presented here is intended to provide competent support for the doctor active in allergology in this work. In the fields of anamnesis, diagnosis and therapy of IgE-mediated allergological illnesses, the quality and certainty of treatment are increased by a structured procedure, complete retrieval of all relevant questions, a matched diagnosis, a therapy implementation in accordance with the ÄDA [Ärzteverband Deutscher Allergologen: Association of German Allergists] guidelines on hyposensitization and complete documentation of all the individual steps. These aims are to be realized with the ALEX Allergy Expert System.

Working together with 5 allergists from the specialist fields of dermatology, ENT, paediatrics, environmental medicine and pneumology, a suitable data-processing system was developed which supports the above-named fields. Through constant updates, ALEX will take account of the latest state of scientific knowledge in allergology.

ALEX is networkable, but can also stand alone, i.e. can be operated without connection to practice management systems. Communication to the PMS is via the BDT interface. Laboratory data are exchanged via an LDT interface. The system based on relational databases has a modular structure. The individual modules are explained briefly below.
Modules of the ALEX Allergy Expert System
1. Practice Management/pre-sets (Section 1)
serves to set practice-specific parameters (type of practice, practice data, test methods, test allergens, therapy methods etc.)
2. Patient Management (Section 2)
to record patient data (manual, chipcard or BDT)
for patient search, among others 3. Anamnesis (Section 3)
Several forms of anamnesis are available (target anamnesis, full anamnesis, "my anamnesis").
Full support is given by the target anamnesis.
All forms of anamnesis are documented.
4. Diagnosis (Section 4)
All common test methods are supported. With the target anamnesis, a test proposal is generated. Anamnesis and test result are made available as a diagnosis proposal. The doctor's confirmation produces the diagnosis.
5. Therapy (Section 5)
A therapy proposal is prepared on the basis of the diagnosis and the pre-set.
In the case of a specific immunotherapy, ALEX leads through several years of therapy, observing the dosage guidelines, dosage schemes and the ADA recommendation, to the SIT.
6. Organization (Section 6)
The organization module manages statistics, transfers patient lists for therapy continuation to the PMS and supports the ordering procedure for therapeutics and test solutions.
Database of allergy sufferers (Section 7)
All recorded data are to be stored in anonymized form in a database. This DB is to display comparable cases at a later date using filters and provide the attending doctor with further information.
1. Practice Management/Pre-Set Module
Each practice working in allergology has individual special features.

Many of these variables must be stored in the system so as to be taken into account in the set of rules.

The pre-set module serves to manage these variables.

The module is password-protected and comprises different headings.

Within these headings the various subject areas are combined into "file cards" for clarity's sake.
2. Patient Management Module The practice management systems currently on the market offer no possibility of the structured, patient-based processing, evaluating and documenting of the information necessary for allergological treatment.

ALEX must therefore manage these data in a suitable form.

For this the inclusion of the patient in the system is indispensable. These tasks are managed in the patient management module.
3. Anamnesis A full anamnesis lies at the heart of allergological diagnosis. Experts are agreed that a thorough anamnesis is half the diagnosis.

Hitherto, pre-prepared questionnaires have been used for this for the most part, e.g. Prof. G. Schultze-Werninghaus's questionnaire. The disadvantage of these questionnaires is that their processing is very time-intensive.

ALEX offers three different forms of anamnesis. All three forms are suitable for a modern allergy diagnosis.

Target anamnesis, a module controlled by means of a complex database-assisted set of rules, is the optimum form of the anamneses offered in ALEX. In a questionnaire algorithm, only the necessary and relevant questions are asked in a targeted and patient-specific manner. Target anamnesis leads to the test proposal. Superfluous questions are suppressed by a logical decision tree, with the result that the time outlay is reduced to a minimum, while the quality of the anamnesis remains the same.

Full anamnesis is an electronic form based on the questionnaire devised by Prof. Schultze-Werninghaus.

An individual questionnaire can be generated from this questionnaire in the pre-sets (see 1.4) which is made available as "my anamnesis".

All three forms of anamnesis are documented in the system as an anamnesis result.

At the start of each of the three available forms of anamnesis, the contraindications relevant for a specific immunotherapy are retrieved via a form.

3.1 Contraindications Check List

Recommendations for specific immunotherapy have been issued by, among others the Ärzteverband Deutscher Allergologen (ÄDA)

the Deutsche Gesellschaft fur Allergologie und klinische Immunologie (DGAI) [German Association for Allergology and Clinical Immunology]

World Health Organization (WHO).

ALEX takes account of the contraindications listed therein in its set of rules via a retrieval which must be processed and confirmed by the attending doctor.

If one or more of the listed contraindications are present, the system issues a corresponding warning.

3.2 Target Anamnesis

In target anamnesis, all the questions are tested for an optimum allergological anamnesis. As questions which are irrelevant for the current patient on the basis of available information are excluded by the stored set of rules, this can be processed much more rapidly than the other offered forms of anamnesis.

The details provided are compared "just in time" via the set of rules with the information from various databases and displayed in an evaluation window at allergen level as a suspicious diagnosis. Exposure period, clinical relevance and any cross-reactivities are evaluated in complex operations.

The central element is an allergen database, unique in this form, currently containing comprehensive information on over 260 allergens. This database is continuously revised and extended. This new knowledge is transferred to ALEX in regular updates.

All information from the target anamnesis is stored in detail at patient level. This makes it possible to reconstruct the anamnesis at any time.

After all the questions have been answered, ALEX prepares an anamnesis result.

The result shows the allergens relevant from the anamnesis sorted according to clinical relevance with the relevant cross-allergens.

This anamnesis result is documented in the system. In addition it can be printed out or otherwise stored as a HTML file.

The target anamnesis concludes with this test proposal, which leads straight into the diagnosis module.

FIG. 1 is an overview table of the anamnesis results in which the substances acting allergenically in the patient concerned are arranged according to their clinical effect.

Figure 2:
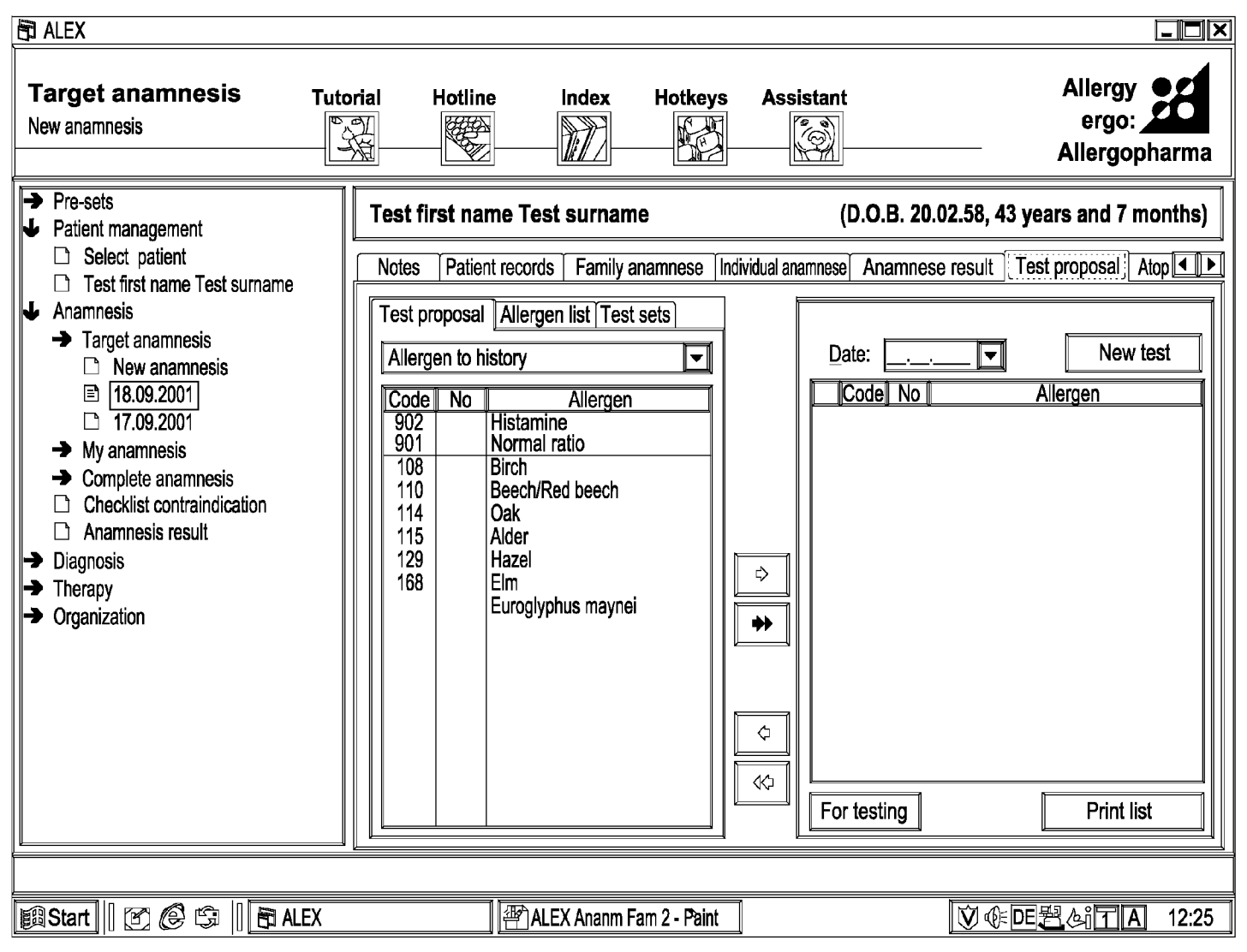

FIG. 2 shows an automatically generated test proposal resulting from the result according to FIG. 1.

My Anamnesis (Children)

My Anamnesis

The module "my anamnesis" calls up the patient questionnaire defined in the default values. With the help of an online form the patient details can be recorded in a simple and time-saving manner. Moreover, a function for printing out the form has been implemented. As a result the questionnaire can also be given to the patient. Based on the completed questionnaire the time required for the actual anamnesis interview is optimized.

3.2.1 Patient Questionnaire

Figure 3:
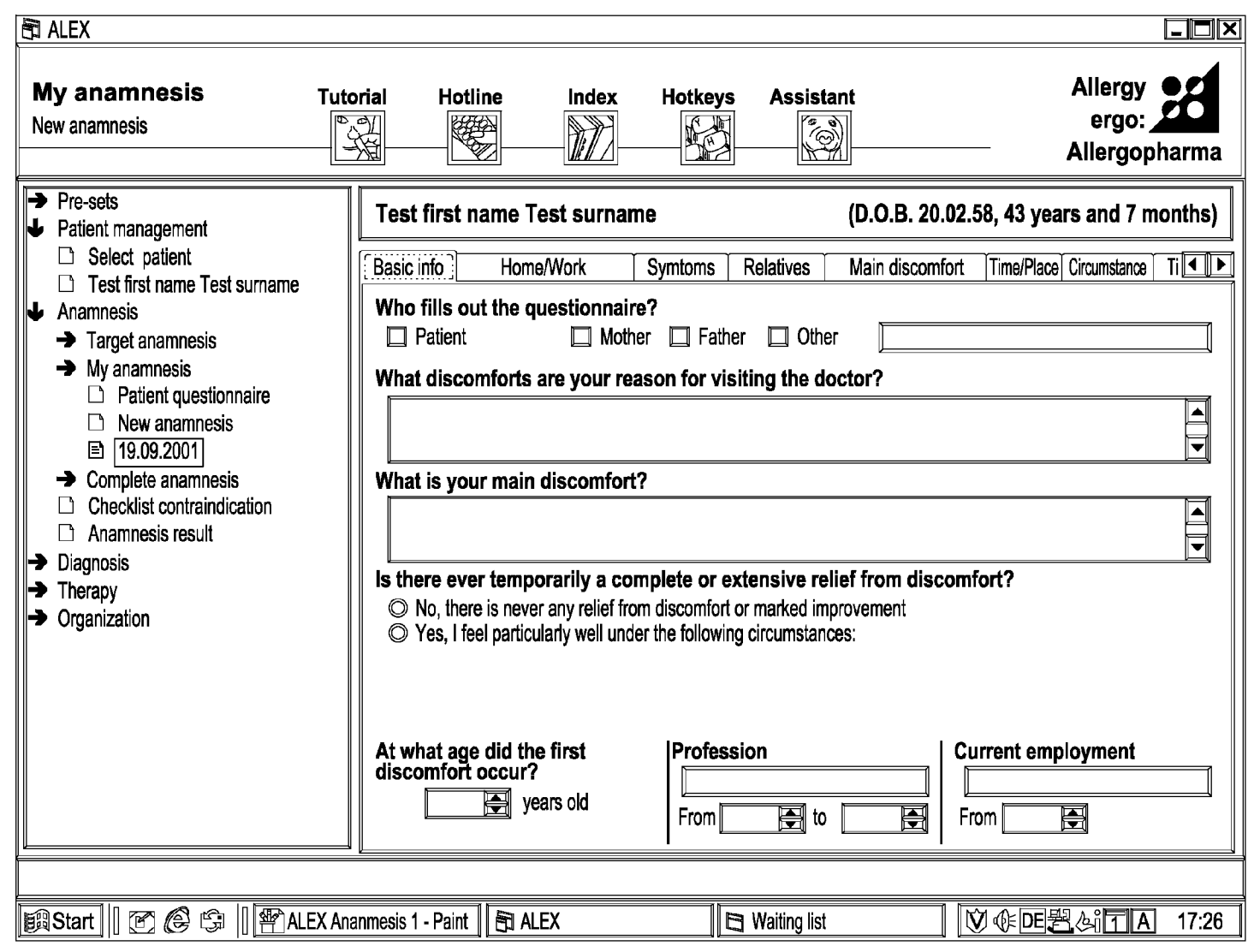

An example of a patient questionnaire is shown in FIG. 3.

The questionnaire is divided into file cards with different subject groups, all of which should be processed if possible.

The set of rules prepares an anamnesis result from the answers.

4. Diagnosis

The allergological diagnosis is made more difficult by the large number of allergens coming into consideration. For this various test methods are available to the doctor working in allergology. Alex supports all established test methods. These test methods are offered according to default value. Via target anamnesis, the system prepares a proposal for the allergens to be tested. This proposal list can be supplemented from various supplementary overviews, depending on the test allergens available in the practice for testing (practice default values).

Thus the doctor can for example complete the test proposal from the overview of the cross-reactive allergens or from stored standard sets. Likewise it is possible to replace proposed allergen combinations with individual allergens.

ALEX shows all the necessary for testing allergens from the target anamnesis. Not all of the allergens listed are available as a standardized test method (e.g. cephalosporin, various types of mites, food or moulds). These allergens are identified in the test proposal. In such cases a possible sensitization by other methods must be clarified (e.g. carence, provocation, scratch or rubbing test).

Test Proposal

The target anamnesis module ends with the test proposal. The test proposal simultaneously leads into the diagnosis module. From the anamnestic data, the ALEX set of rules calculates a test proposal in which all the allergens suspected of sensitization are listed. The deliverable test allergens are provided with their codes. Allergens for which there are no test substances must possibly be further clarified anamnestically or tested by other means (e.g. carence in the case of food).

4.1 Testing

The test module shows as file cards the test methods stored in the default values as being available in the practice.

Once the corresponding file card has been selected, the test results can be recorded.

FIG. 4 shows the screen representation of a corresponding file card which reproduces the test result.

4.2. Diagnosis Proposal

In the diagnosis proposal all the data hitherto available from anamnesis and all tests carried out are processed and displayed in easily understood form in a diagnosis proposal.

For the diagnosis, however, only those allergens for which the test results significantly display a possible sensitization are proposed, i.e. the test results must lie significantly above those of the control measurements.

Finally, FIG. 5 shows the screen representation of the diagnosis proposal deduced automatically from the anamnesis and from the test results.

5. Therapy

Specific immunotherapy (hyposensitization, desensitization, allergy inoculation) is the only causal therapy for the treatment of type I allergies.

The complexity of the anamnesis and diagnosis also continues in the therapy. The doctor working in allergology is faced with the task of formulating, from a large number of possible allergen formulations, the therapy solution matched to the diagnosis.

Specific immunotherapy is also much more time-consuming and complicated to implement than most other therapies in medical practice. Patient-tailored dosages according to predetermined dosage guidelines must be borne in mind, injection frequencies maintained and "brief anamneses" carried out prior to each injection.

Specific immunotherapy is therefore to be carried out only by allergologically experienced doctors.

The ALEX Allergy Expert System also supports the doctor in this task. A complicated set of rules and control system which documents all the treatment steps in detail actively accompanies the doctor actively through this demanding therapy.

The recommendations issued by the umbrella organizations are taken into account as minimum requirements.

ALEX prepares a therapy proposal on the basis of the diagnosis.

This proposal takes into account all the rules regarding the composition of allergen extracts for specific immunotherapy.

In the case of a house-dust or flour mite allergy, carence measures can support immunotherapy.

5.1 Consent Form

Specific immunotherapy requires a patient consent form.

5.2 Therapy Proposal

A complex program takes all guidelines into account in the preparation of the therapy proposal.

Only seasonal allergens are suggested in combination.

To avoid a dilution effect, only allergen mixtures with a maximum of 4 individual allergens are supplied.

Approved pre-prepared drugs are preferred.

5.3 Therapy Monitoring

The unambiguous guidelines for carrying out a specific immunotherapy are monitored by a complex control system.

Prior to each injection a brief anamnesis must take place without which an injection cannot be carried out. All information relating to each individual injection is documented in detail.

The required monitoring time of 30 minutes is controlled, monitored and documented via a suitable module.

Dose reductions on the basis of various circumstances, e.g. unexpected allergen exposure or delay in the injection intervals, are calculated, displayed and documented.

As a result an optimum organizational therapy certainty is achieved.

6. Organization

The organization of the allergological practice is supported by the "to-do list" module. The system monitors all the relevant deadlines and stock levels.

Necessary measures are displayed automatically and their implementation supported by a stored work-flow (e.g. mail-merge letters etc.).

6.1 Recall Service

Patients who have completed the first or subsequent therapy years but whose therapy is not yet finished are placed in the recall system.

Compliance is to be thereby controlled so that premature therapy interruptions are prevented and the success of the therapy optimized.

The system uses the documented data to suggest patient-tailored deadlines for follow-up therapy.

6.2 Mail-Merge Letters Function

The organization module contains a mail-merge letters function which makes it possible to produce various documents.

6.3 Standard Documents

Using this function, standard documents can be devised and produced into which the corresponding data from the patient file can be incorporated (e.g. diagnoses, test results).

These standard documents are to provide support e.g. in the preparation of expert opinions.

6.4 Statistics

A statistics tool gives the doctor information on his allergological work at all times.

6.5. Allergy Sufferers database

As all patient data are present in structured and compressed form, a database can be fed from this information.

These data are stored in anonymized form on a protected server to which the connected practices then have access.

As a result it is possible to compare in-house patient cases with comparable cases of other allergists and to compare information from same for a therapy.

In other words, this means that on the basis of a completed anamnesis, comparable anamneses can be selected from the system. These patient cases display test results and therapies with corresponding therapy success parameters which can then serve the doctor as a decision-forming basis for his tests, diagnosis and therapy.

The system can draw conclusions from the stored discomfort profiles (discomfort period, symptoms etc.) and automatically readjust, e.g.:

The discomfort period for betula sensitizations moves from April/May to March/April. The system can then be adjusted as regards the test, diagnosis and therapy proposals.

It is planned to put the whole system on the Internet in the future so that further information can be exchanged.

The invention claimed is:

1. A method wherein a computer processor is used for recording and analyzing syndromes of allergic diseases and their causes and for establishing appropriate therapy proposals comprising a) preparing at least one set of anamnesis questions, wherein the anamnesis questions include questions relating to the time or cause of the occurrence or a combination thereof, the severity of symptoms of an allergic disease and the environmental exposure of a patient, and storing this set in a data memory in a tangible computer-readable media, b) preparing a set of data relating to the causes of allergic diseases, including a listing of allergens, and storing this set in a data memory in a tangible computer-readable media, wherein the data is continuously revised and extended, c) providing a computer program which selects and presents anamnesis questions according to a predetermined set of rules, d) recording the answers to the anamnesis questions in a tangible computer-readable media, wherein within the framework of the anamnesis questions preliminary information is recorded which includes at least the age and gender of a patient and optionally one or more principal allergic symptoms, affected organs or other diagnosed illnesses or a combination thereof, and wherein the answers are at least partly predetermined in discrete selection steps, e) awarding point values to at least some of the answers to anamnesis questions, f) adding or multiplying together the point values for specific answers or groups of answers, thereby creating total point values for a group of answers or the entire anamnesis or a combination thereof, and storing the total point values in a data memory in a tangible computer readable media, g) creating a set of possible diagnoses using the criterion of whether the total point values for specific groups of answers or the entire anamnesis or a combination thereof exceed a predeterminable threshold value and preparing a proposal for the allergens to be tested to further narrow down the diagnosis, h) preparing one or more diagnosis proposals, i) preparing one or more therapy proposals, wherein steps e) to i) proceed automatically under the control of an interactive computer program, which outputs or displays the questions, diagnoses or proposals or a combination thereof, j) preparing test proposals to further narrow the diagnosis proposals and therapy proposals, k) providing a storage device in which all the data recorded from patients is supplied in anonymized form, and l) selecting comparable anamneses from the data recorded from patients based on the answers to the anamnesis questions.

2. A method according to claim 1, wherein g) includes the comparison of the obtained set of answers with other sets of answers which have been obtained from earlier anamneses.

3. A method according to claim 1, wherein contraindications are recorded prior to the preparing of therapy proposals.

4. A method according to claim 1, wherein contraindications are recorded prior to the preparing of therapy proposals within the framework of d).

5. A method according to claim 1, wherein the computer program has a scale valuation and combination of the scale valuations of individual answers for the analysis of the recorded data.

6. A method according to claim 1, which is performed or operated on a computer that is without connection to a network.

7. A system in a tangible computer-readable media wherein a computer processor is used for recording and analyzing syndromes of allergic diseases and their causes and for establishing appropriate therapy proposals comprising a) a data memory with a stored set of anamnesis questions in a tangible computer-readable media, wherein the anamnesis questions include questions relating to the time or cause of the occurrence or a combination thereof, the severity of symptoms of an allergic disease and the environmental exposure of a patient, b) a stored set of data in a tangible computer-readable media relating to causes of allergic diseases, including pathogenic or allergenic substances or a combination thereof, wherein the data is continuously revised and extended, c) a computer with a computer program which is capable of evaluating and presenting anamnesis questions according to a predeterminable set of rules, d) an input device for the inputting of patient data and answers to the anamnesis questions, wherein the answers are at least partly predetermined in discrete selection steps, e) a storage device for the inputted data in a tangible computer-readable media, f) a computer program in a tangible computer-readable media which processes the inputted data for the purpose of creating proposals for allergens to be tested, one or more diagnoses and one or more therapy proposals, wherein point values are awarded to at least some of the answers to anamnesis questions and wherein the point values for specific answers or groups of answers are added or multiplied together, thereby creating total point values for a group of answers or the entire anamnesis or a combination thereof, g) an output device for the presentation of the questions, the diagnoses or therapy proposals or a combination thereof, h) said output device being capable of further presenting test proposals for the allergens to be tested to further narrow the diagnosis proposals and therapy proposals, and i) wherein a storage device is provided in which all the data recorded from patients is supplied in anonymized form for comparison of anamneses.

8. A system according to claim 7, wherein the storage device with anonymized patient data is a storage device which is accessible to a specifiable circle of users.

9. A system according to claim 7, which has an access possibility to an allergen database.

10. A system according to claim 7, wherein the computer program in f) has a scale valuation and combination of the scale valuations of individual answers for the analysis of the recorded data.

11. A system according to claim 7, wherein the program in f) has a module which carries out a comparison with recorded anamnesis data available in the system for the analysis of the recorded data.

12. A system according to claim 7, which is without connection to a network.

* * * * *